United States Patent [19]

LaRue

[11] Patent Number: 5,156,298
[45] Date of Patent: Oct. 20, 1992

[54] METHOD AND APPARATUS FOR DETECTING A LIMIT OF THE USABLE PORTION OF A BATCH OF FLUENT MATERIAL FLOWING IN A CONDUIT

[75] Inventor: Joseph P. LaRue, Holly, N.Y.

[73] Assignee: Eastman Kodak Company, Rochester, N.Y.

[21] Appl. No.: 684,530

[22] Filed: Apr. 11, 1991

[51] Int. Cl.⁵ .............................. B67D 5/08
[52] U.S. Cl. ...................... 222/66; 222/52; 222/129; 222/144.5
[58] Field of Search .............. 222/1, 52, 66, 129, 222/144.5; 324/445, 446

[56] References Cited

U.S. PATENT DOCUMENTS

| | | | |
|---|---|---|---|
| 3,770,020 | 11/1973 | Tamura et al. | 137/802 |
| 3,810,778 | 5/1974 | Wang | 222/1 X |
| 4,134,059 | 1/1979 | Stankoff | 324/29 |
| 4,137,495 | 1/1979 | Brown | 324/30 |
| 4,282,487 | 8/1981 | Warren et al. | 324/445 |
| 4,467,941 | 8/1984 | Du | 222/1 |
| 4,484,582 | 11/1984 | Rottenberg et al. | 128/630 |
| 4,491,798 | 1/1985 | Palmer et al. | 324/425 |
| 4,580,096 | 4/1986 | Liedholz | 324/445 X |
| 4,590,431 | 5/1986 | Anderson et al. | 324/445 X |
| 4,788,852 | 12/1988 | Martin et al. | 73/61.1 R |
| 4,810,963 | 3/1989 | Blake-Coleman et al. | 324/204 |
| 4,820,990 | 4/1989 | Moore | 324/445 |

FOREIGN PATENT DOCUMENTS 0235437  9/1987  European Pat. Off. .......... 222/144.5

Primary Examiner—Andres Kashnikow
Assistant Examiner—Joseph A. Kowfman
Attorney, Agent, or Firm—Carl F. Ruoff

[57] ABSTRACT

Method and apparatus for detecting a limit of a usable portion of a batch of fluent material flowing in a conduit from a container wherein usable and unusable material lie in layers. The embodiment disclosed includes two containers each having a conduit leading from the container to a switching valve. Each conduit is provided with a sensor for sensing the conductivity of fluent material flowing in the conduit. Signals from the sensors are sent to a computer which has in memory a range of values for the conductives of usable material. When the signal from a sensor goes outside that range the computer generates a signal to the switching valve to cause the switching valve to discontinue flow from the one container and allow flow from the other container which contains a fresh batch of fluent material. A conduit leads from the switching valve to a coating hopper for coating a thin layer of photographic emulsion on a continuous web. The unusable material may be froth on top of the usable material or it may be air. The leading or trailing end of a flow of fluent material in a conduit may be detected.

3 Claims, 3 Drawing Sheets

METHOD AND APPARATUS FOR DETECTING A LIMIT OF THE USABLE PORTION OF A BATCH OF FLUENT MATERIAL FLOWING IN A CONDUIT

FIELD OF THE INVENTION

This invention relates to the detection of a limit of a usable portion of a batch of fluent material flowing in a conduit from a container. Such usable portion may be the whole of the batch or it may be the portion other than an unusable portion with the usable and unusable portions lying in layers in the batch in the container. The unusable portion may be usable for a purpose other than that for which the usable portion is intended.

BACKGROUND OF THE INVENTION

Photosensitive emulsion for coating on a substrate, such as, for example, a continuous web of paper, cellulose acetate or polyethylene terephthalate, is manufactured in a container. It is drawn from the container through a conduit, usually leading from the bottom of the container, which supplies the emulsion to a coating hopper which applies the emulsion as a uniform thickness layer to the substrate. It is known that in the manufacture of the emulsion in the container, a layer of unusable material, such as froth, usually forms on top of the usable material. The froth is unusable because there must be no air bubbles in the emulsion supplied to the hopper for coating on the substrate. Thus, it is important that when the emulsion is being drawn from the container and supplied through the conduit to the hopper, the unusable material not be supplied to the hopper.

In practice, as the supply of emulsion from one container is approaching depletion, the flow from that container is discontinued but continuity of feed of good emulsion to the hopper is achieved by switching to another similar container containing a new, full batch of emulsion. At present the switching is performed on the basis of the level of material in the container approaching depletion. It is known that with such a method of determining when to switch the supply to the hopper from one container to another, there is considerable waste of usable material in the container being superseded. As is known, some of the materials used in making photographic emulsions are very costly and such waste of usable material represents a very great expense.

In situations when there is not a layer of unusable material lying on top of the usable material in the container, the supply from the first container cannot be totally drawn down through the conduit to be followed by switching to supply from a second container. If such a procedure were allowed there would be the problem of air flowing to the hopper behind the last of the emulsion from the first container and ahead of the beginning of the flow of emulsion from the second container. Such a procedure would allow air into the hopper, which is unacceptable. Thus, in such situations also, for safety's sake, switching between containers has occurred when there is still usable emulsion left in the first container. Such usable emulsion left in the container becomes expensive waste.

It is an object of the present invention to reduce waste.

SUMMARY OF THE INVENTION

According to the present invention waste is substantially reduced by providing a method of detecting a limit of the usable portion of a batch of fluent material flowing in a conduit from a container. The method of the invention includes sensing the electrical conductivity of the material in the conduit with an electrical conductivity testing device adapted to provide a first signal indicative of the conductivity of the material in the conduit, determining a range of values of the first signal indicative of the presence of usable material in the conduit, and providing a second signal when the first signal is outside the range.

The second signal may be used to cause switching from the container supplying the fluent material flowing through the conduit to a second container containing a batch of fluent material.

An embodiment of the present invention will now be described, by way of example, with reference to the accompanying drawings, in which:

DESCRIPTION OF THE PREFERRED EMBODIMENT

Figure 1:
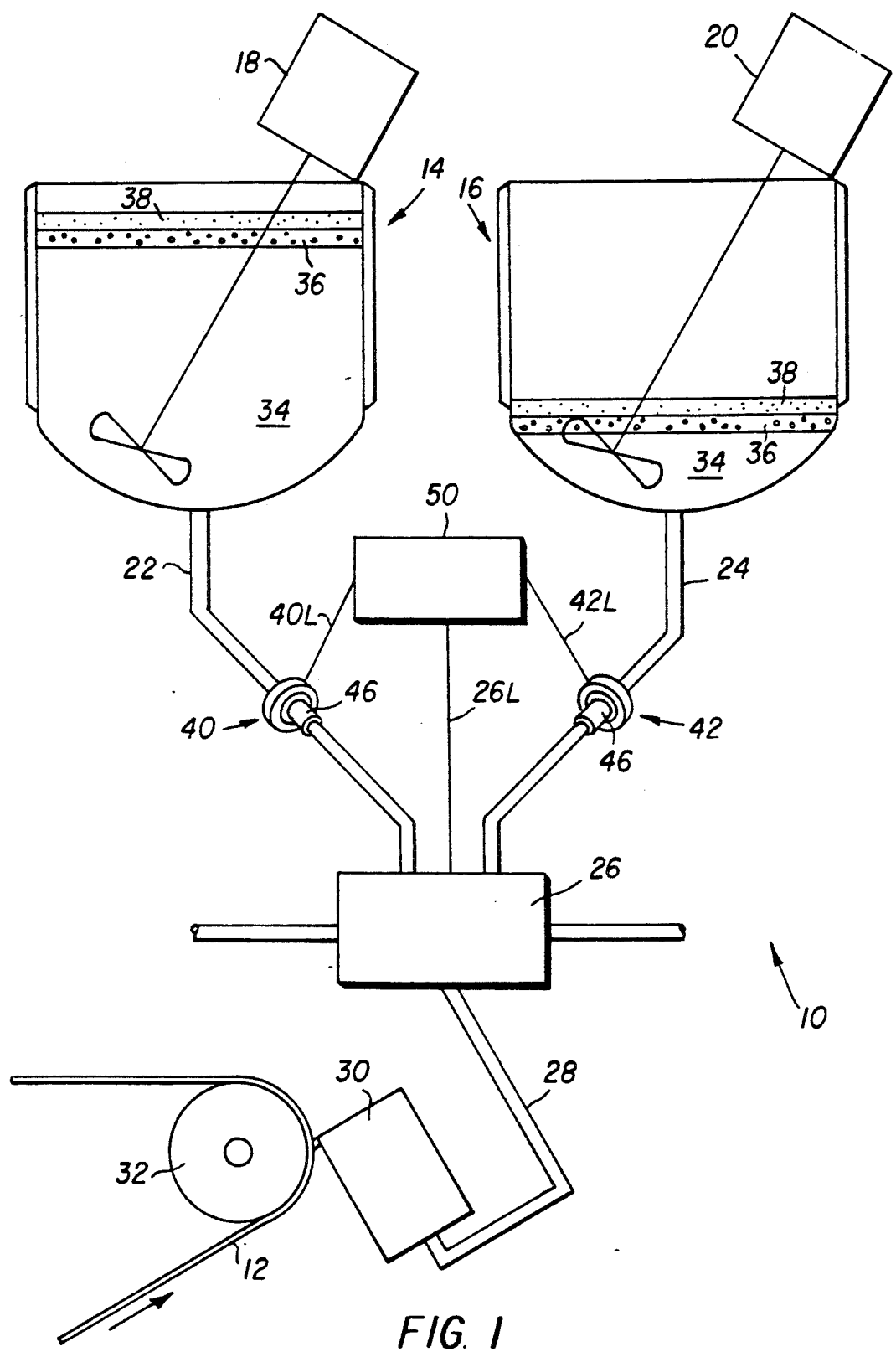
FIG. 1 is a schematic representation of a photographic coating hopper and a system for supplying emulsion to the hopper, including an embodiment of the present invention.

In FIG. 1 of the accompanying drawings there is illustrated, schematically, apparatus 10 for manufacturing photographic emulsion and for coating it on a web 12 of paper. The apparatus 10 includes two identical containers 14 and 16 in which emulsion, a fluent material, is manufactured. Associated with each container 14, 16 is a stirrer 18, 20, respectively. Extending from the bottom of each container 14, 16 is a conduit 22, 24 respectively. Flow of emulsion out of a container into its conduit is controlled by a valve, not shown.

Both of the conduits 22, 24 lead to a switching valve 26. A third conduit 28 leads from the switching valve 26 to a hopper 30. The hopper 30 is located adjacent a support roller 32 which serves to position the web 12 in position adjacent the hopper 30 during a coating operation.

The switching valve 26 serves to select which conduit 22 or 24 is in communication with the third conduit 28 and, hence, determines which container 14 or 16 is, at any particular time, supplying emulsion to the hopper 30.

Emulsion 34 to be coated on the web 12 is manufactured in the containers 14, 16. The manufacture of photographic emulsion is well known to those skilled in the art and does not form part of the present invention. Further description of it will not be given herein. As illustrated in FIG. 1, container 16 is supplying emulsion 34 to the hopper 30 and the emulsion in the container 16 is approaching depletion. It will be observed that on top of the emulsion 34 there are layers 36 and 38 of froth, the layers 36 and 38 being of different density. The froth in the layers 36, 38, by definition, contains air bubbles. Those skilled in the art of coating know that air bubbles must not be allowed to enter the hopper 30, let alone be coated on the web 12.

The switching valve 26 is used to switch supply from one container, when the emulsion therein is close to being depleted, to the other container in which a new batch of emulsion has been made and is waiting to flow to the hopper.

The prior art has determined when switching from one container to another should occur by detecting the level of the emulsion in the container. It is known to use a dip tube for the purpose of detecting the level in the container. Such a method of determining when to switch has caused large amounts of usable emulsion to be wasted because the switch has been made at a very conservative stage of depletion of emulsion in the container in order to avoid the very severe problems associated with air bubbles getting into the hopper. The conservatism is determining when to switch supplies has been dictated because of the froth layers and the lack of knowledge of their depths and the fact that, the bottoms of the containers being rounded, the rate of change of surface level increases rapidly, even though outflow rate is constant, as the surface approaches the bottom. Furthermore, the penalty for a late or non-existent signal to switch between supplies is that air will get into the hopper. This requires a complete shutdown of the operation and purging of the equipment as well as waste of emulsion waiting to be coated.

Figure 2:
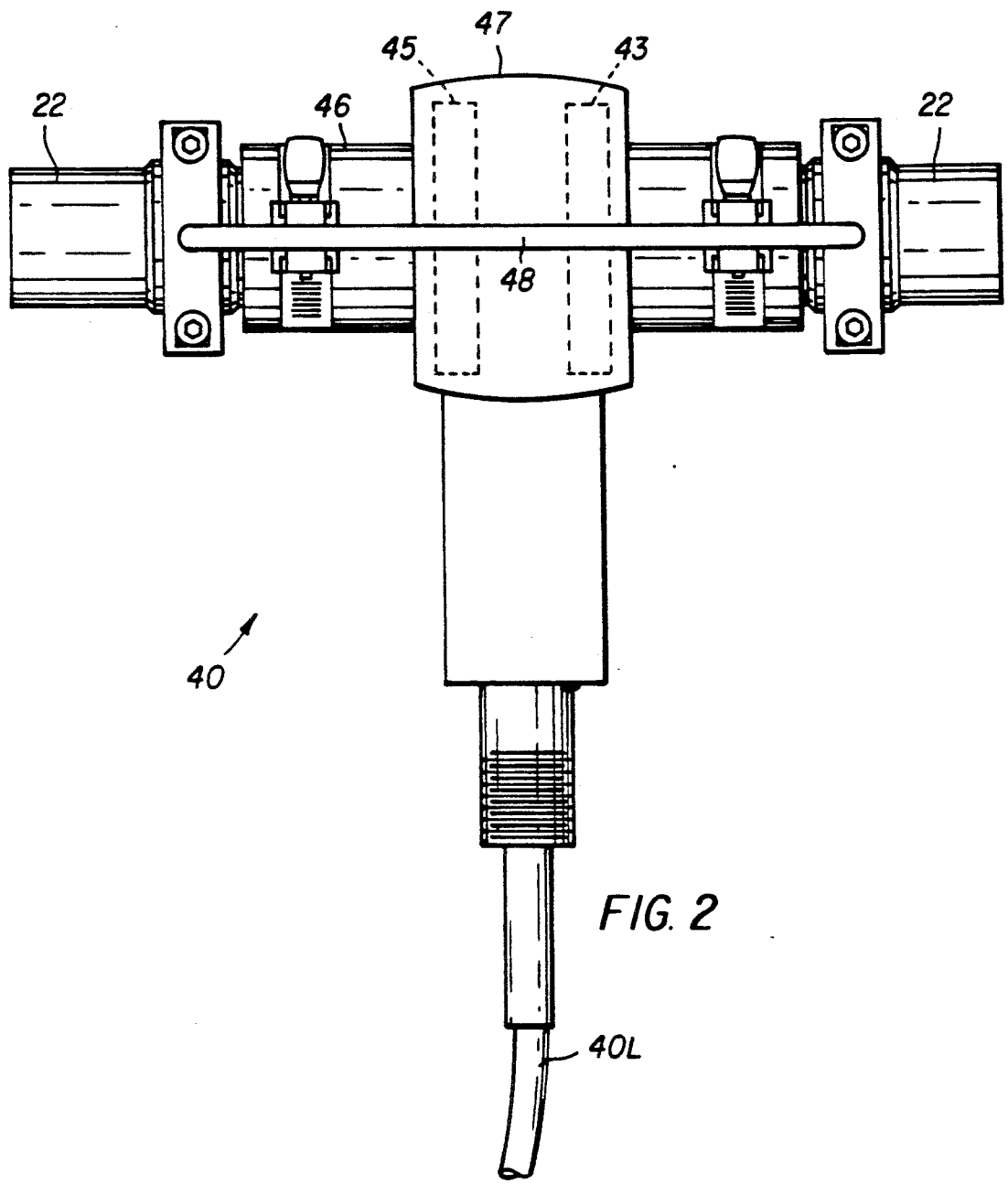
FIG. 2 is a plan view of a sensor used in the apparatus illustrated in FIG. 1.

According to the present invention, there is associated with each conduit 22 and 24, a sensor 40, 42, respectively. The two sensors are identical and one of them is illustrated in FIG. 2. Each sensor is intended for use in determining the conductivity of the fluent material, the emulsion, flowing through it. It is a modification of a sensor manufactured by Foxboro Instrument Corporation under the model number 871 AB-3. The sensor comprises two toroidal coils (shown in broken lines in FIG. 2 and given the reference numerals 43 and 45, respectively) having their axes aligned and spaced apart axially. One coil is a transmitter and the other is a receiver. The two coils 43 and 45 are located within toroidal housing 44. Disposed coaxially within the coils and housing 44 is a tube 46 formed of electrically non-conductive material. The conduits 22 and 24, formed of stainless steel, are discontinuous at the associated sensor and the non-conductive tube is sealingly connected to the ends of the conduit to bridge the discontinuity. A strap 48 of electrically conductive material electrically connects the two portions of the electrically conductive conduit 22. Further description of the sensor 40 will not be given because its principal of operation is well known. Suffice it to say that a current is passed through one of the coils. It creates a field in the emulsion flowing in the tube 46, this being possible because the tube is non-conductive. A field is created within the second coil, the strength of which is dependant on the conductivity of the emulsion. The field within the second coil generates a current therein, the magnitude of which is used as an indication of the conductivity of the emulsion.

The two sensors 40 and 42 are connected to a computer 50 by leads 401 and 421, respectively. Stored within the computer is a range of values which represents values of the conductivity of emulsion when it is acceptable for coating. It will be recognized that the conductivity of emulsion froth is different to the conductivity of emulsion free of air bubbles, so that it is possible to use conductivity as a metric for determining acceptability or unacceptability for coating. Thus, when the measured value of the conductivity of the emulsion within the tube 46 goes outside the range of acceptable values, it can be taken that the emulsion is no longer usable for coating. At such time the computer sends a signal, through lead 261, to the switching valve 26 to close off flow from the conduit 22 or 24, which, at the sensor in the conduit, now contains unusable emulsion, and to open flow from the other conduit 24 or 22 leading from the vessel containing the freshly prepared batch of emulsion.

It will be observed that the sensors 40 and 42 are spaced along the conduits 22 and 24 away from the switching valve 26 so that even if the emulsion which precedes that which causes the computer to send a switching signal, is marginally unsatisfactory, it has not reached the switching valve by the time switching occurs, and hence such marginally unacceptable emulsion will never reach the hopper. Furthermore, should there be no unusable material on top of the usable emulsion in the vessel (in other words, air is following the usable emulsion in the conduit), the sensor will provide a signal along line 261 to cause switching, when the trailing end of the flow of usable emulsion is passing the sensor and air is in the tube in the sensor. Thus, the signal to switch has been sent by the computer, and acted on by the switching valve, before the trailing end of the flow of usable material reaches the switching valve, and, more importantly, before air can reach the switching valve 26 and get passed on to the hopper.

In FIG. 1, conduits additional to the conduits 22, 24 and 28 are shown extending from the kettle switching valve. These additional conduits are for cleaning water and waste and form no part of the present invention and will not be further described, except to say that the computer may also control flow through them for flushing one or the other of the conduits 22 and 24 which has just been brought out of supply service.

It will be recognized that the volume of usable emulsion which is wasted each time the switching valve switches from taking supply from one container to taking supply from the other container is approximately the volume of the length of conduit between the sensor and the valve. It will further be recognized that the volume of such length of conduit is markedly less than the volume of the entire conduit from the container to the valve plus the volume of the emulsion in the bottom of the container at the time the prior art system decided that switching between containers should occur.

In the description above, an embodiment of the invention is used to cause switching of source of emulsion when unusable material is following usable material along the conduit, the unusable material having been in a layer over the usable material in the vessel. In such case the limit of the usable portion is at the juncture of the usable and unusable portions. It was mentioned above that the invention is applicable also for detecting the end of usable material when it is followed directly by air, there being no contiguous unusable material. In such case the limit of the usable portion of the material is at the trailing end of the flow of material.

It will be understood that the invention is also applicable for detecting the leading end of a flow of usable fluent material in a conduit whether the usable material is preceded by unusable material or air. Furthermore, it is to be understood that as used herein the term unusable material is intended to mean that the material is unusable for the purpose for which the usable material is intended.

Figure 3:
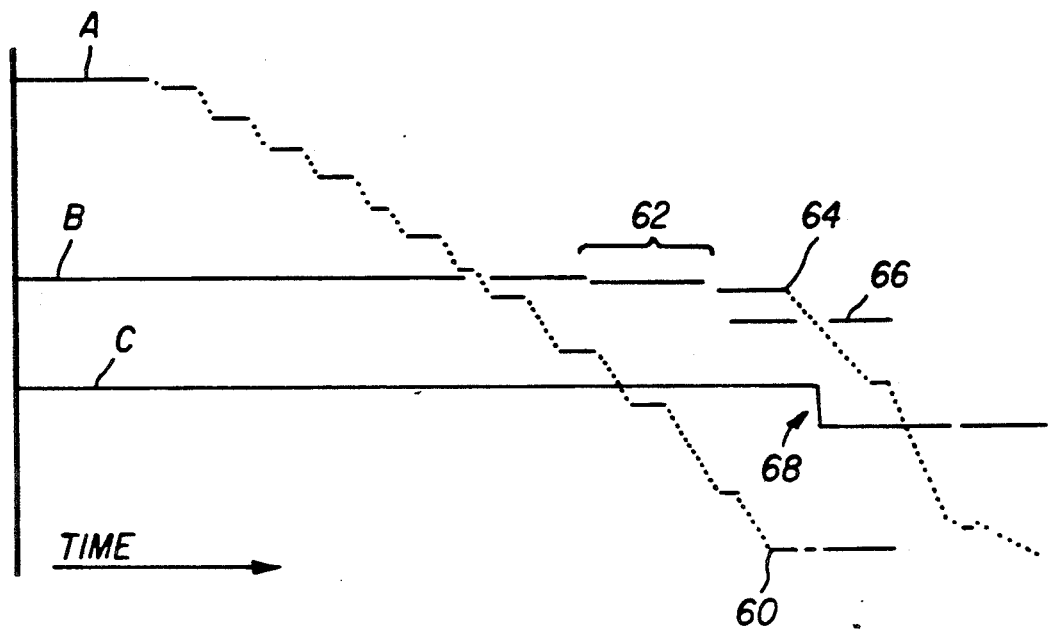
FIG. 3 is a plot showing drop in level of fluent material in a container, the conductivity of the fluent material sensed by the sensor, and the generation of a signal, in an example in which there is unusable material in a layer over usable material in the container.
Figure 4:
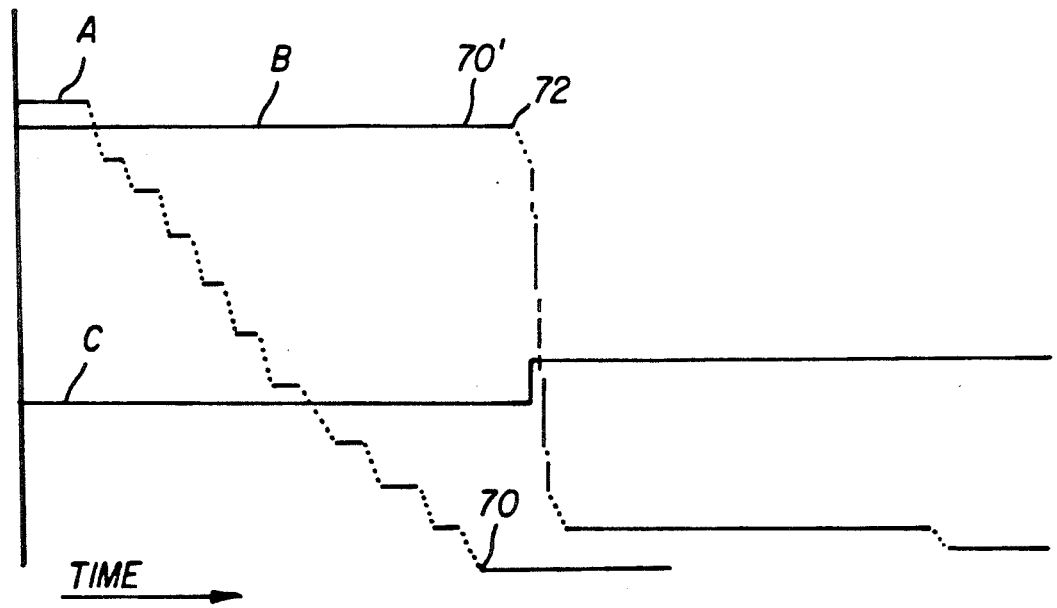
FIG. 4 is a plot similar to that in FIG. 3, but for an example in which there is no unusable material over the usable material and air follows the usable material in the conduit.

FIGS. 3 and 4 are plots showing:
A—container level;
B—conductivity of fluid material in sensor;
C—switch signal.

The plots illustrated in FIG. 3 are representative of a case in which there is a layer of unusable material, for example, froth, on top of the layer of usable material in the container. It will be observed that the level of fluent material, emulsion and froth, represented by plot A, steadily declines with time and after point 60 the vessel is empty. The vessel being empty means that all of the usable emulsion as well as the unusable froth has entered the conduit leading to the switching valve and on the way to which it passes through the sensor. It will be seen from plot B, which shows the conductivity of fluid material instantaneously within the sensor, that even before the container is empty, the conductivity is dropping slightly with time (see the region 62). This is indicative that the nature of the material flowing through the sensor has changed slightly. However, from experiment, it is known that the material, namely the emulsion, is still perfectly satisfactory for coating. After point 64, when the container is empty, the rate of change of conductivity increases. The value of the conductivity at which the computer generates a signal to cause switching of the flows may be identified as a percent of baseline deviation or absolute value. From prior experiments it has been found that when the conductivity has dropped to value defined by line 66, the emulsion is no longer satisfactory for coating. Thus, conductivity defined by line 66 is taken as the lower limit of a range of conductivity values which are acceptable; e for the material to be used for coating and the computer generates a signal causing the switching valve to switch. Plot line C shows the switch signal being given at 68.

FIG. 4 illustrates a situation in which there is no froth on the emulsion in the container. Thus, as the last of the usable emulsion flows out of the container, it is followed into the conduit by air. Plot A again shows the level of emulsion in the container falling until the container is empty after point 70. The emulsion to air interface takes some time to flow down the conduit and reach the sensor, witness the fact that conductivity (plot B) does not start dropping off, at point 72, for some time after point 70' which is at the same time as point 70. As is to be expected, with an emulsion to air interface at the trailing end of the usable emulsion flowing in the conduit, the conductivity drops precipitously as the interface passes the sensor. The switch signal (plot C) may be generated on an absolute magnitude of conductivity signal drop or it may be generated at a particular value.

In the foregoing description it has been said that the signals from the sensors are passed to a computer and that it is the computer which generates a signal for causing switching of the supplies. The term computer is to be understood in a very broad sense and is to be taken as including the sensors including a local transmitter monitor, that is, an on-board low signal monitor relay; or a programmable logic controller, for example.

While the invention has been described in detail and with reference to specific embodiments thereof, it will be apparent to one skilled in the art that various changes can be made therein without departing from the spirit and scope thereof.

What is claimed is:

1. An apparatus for supplying fluent photographic material to a coating station consisting of:
   switching means;
   a first container for containing fluent photographic material;
   a first conduit leading from said first container to said switching means;
   first means for sensing the electrical conductivity of fluent photographic material flowing in said conduit from said first container and for providing a first signal related to said conductivity;
   a second container for containing fluent photographic material;
   a second conduit leading from said second container to said switching means;
   second means for sensing the electrical conductivity of fluent photographic material flowing in said conduit from said second container and for providing a second signal related to said conductivity;
   a third conduit leading from said switching means;
   said switching means being adapted to switch flow from either said first or said second conduit to said third conduit; and
   means for causing said switching means to switch in response to a signal from said first or said second means for sensing conductivity.

2. An apparatus for supplying fluent photographic material consisting of:
   switching means;
   a first container for containing fluent photographic material;
   a first conduit leading from said first container to said switching means;
   first means for sensing the electrical conductivity of fluent photographic material flowing in said conduit from said first container and for providing a first signal related to said conductivity;
   a second container for containing fluent photographic material;
   a second conduit leading from said second container to said switching means;
   second means for sensing the electrical conductivity of fluent photographic material flowing in said conduit from said second container and for providing a second signal related to said conductivity;
   a third conduit leading from said switching means;
   said switching means being adapted to switch flow from either said first or said second conduit to said third conduit;
   means for causing said switching means to switch in response to a signal from said first or said second means for sensing conductivity;
   a hopper for forming fluent photographic material into a layer for applying to a continuous substrate;
   said third conduit leading to said hopper.

3. An apparatus for supplying fluent photographic material to a coating station consisting of:
   switching means;
   a plurality of containers for containing fluent photographic material;
   a plurality of conduits leading from said plurality of containers to said switching means;

a plurality of sensing means for sensing the electrical conductivity of fluent photographic material flowing in said plurality of conduits from said plurality of containers and for providing a plurality of signals related to said conductivities;

an exit conduit leading from said switching means to the coating station;

said switching means being adapted to switch flow from one of said plurality of conduits to said exit conduit; and means for causing said switching means to switch in response to a signal from said plurality sensing means.

* * * * *